(12) United States Patent
Kim et al.

(10) Patent No.: US 9,573,894 B1
(45) Date of Patent: Feb. 21, 2017

(54) ENERGETIC N-SUBSTITUTED 3, 3-DINITROAZETIDINE PLASTICIZER AND PREPARATION METHOD THEREOF

(71) Applicant: AGENCY FOR DEFENSE DEVELOPMENT, Daejeon (KR)

(72) Inventors: Seung-Hee Kim, Daejeon (KR); Jinseuk Kim, Daejeon (KR); Chang-Woo Cho, Daegu (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 14/844,377

(22) Filed: Sep. 3, 2015

(51) Int. Cl.
C07D 205/04 (2006.01)

(52) U.S. Cl.
CPC .................. *C07D 205/04* (2013.01)

(58) Field of Classification Search
None
See application file for complete search history.

(56) References Cited

PUBLICATIONS

CAPLUS printout of "Foreign Patent No. KR1496681" published on Mar. 4, 2015.*

* cited by examiner

*Primary Examiner* — Matthew Coughlin
*Assistant Examiner* — Po-Chih Chen
(74) *Attorney, Agent, or Firm* — LRK Patent Law Firm

(57) ABSTRACT

N-substituted 3,3-dinitroazetidine, represented by the following Chemical Formula I, as an energetic plasticizer, and a method for preparing the same through a coupling reaction in which the energetic material 3,3-dinitroazetidine or an acid salt thereof serves as a nucleophile for the α,β-unsaturated carbonyl compound as a substrate are provided.

[Chemical Formula I]

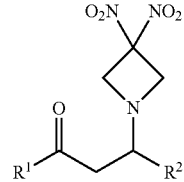

wherein $R^1$ and $R^2$ are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom, wherein the substituent of the substituted radicals is selected from the group consisting of alkyl, cycloalkyl, aryl, heteroaryl, alkoxy, thioalkyl, amino, nitro, hydroxy, a halogen atom, and a combination thereof.

3 Claims, 5 Drawing Sheets

ENERGETIC N-SUBSTITUTED 3,3-DINITROAZETIDINE PLASTICIZER AND PREPARATION METHOD THEREOF

BACKGROUND OF THE INVENTION

1. Technical Field

The present invention relates to N-substituted 3,3-dinitroazetidine as a high-performance, energetic plasticizer, and a method for preparing the same.

2. Description of the Related Art

Plastic-bonded explosives have been developed to improve both the performance and insensitivity of explosives. Generally, a plastic-bonded explosive consists of a granular explosive, responsible for explosive power, such as RDX (Research Department Explosive), and a binder system. The binder system is used in an amount of about 2~20% by weight based on the total weight of the plastic-bonded explosive, and functions to provide dimensional stability and insensitivity for the granular explosive. Lacking a nitro group, which plays an essential role in explosive performance, however, the binder system degrades the overall performance of the explosive.

To maximize the performance of plastic-bonded explosives, extensive research has been directed toward the introduction of a nitro group into a plasticizer. A nitro group-introduced plasticizer is called an energetic binder or plasticizer. The high energetic plasticizers bis(2,2-dinitropropoxy)methane (Chemical Formula 1) and N,N'-methylenebis(N-methylnitramide) (Chemical Formula 2) make a great contribution to the performance of plastic-bonded explosives, but are highly sensitive. Further, formal/acetal-based plasticizers (F/A plasticizers), which use two different plasticizers, as shown in Chemical Formula 3, may be prone to dissociation of the components during long-term storage.

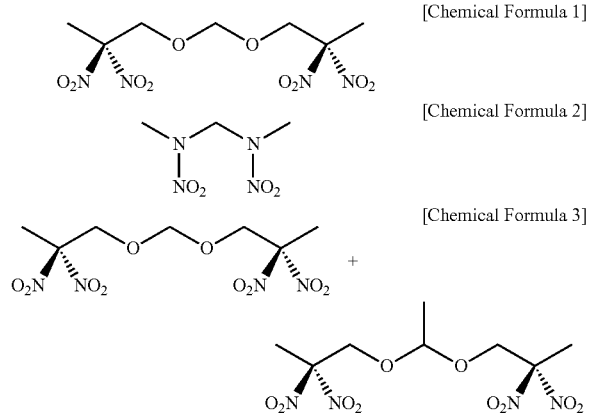

[Chemical Formula 1]

[Chemical Formula 2]

[Chemical Formula 3]

SUMMARY OF THE INVENTION

With the problems encountered in the related arts in mind, the present inventors found that the high sensitivity of plastic-bonded explosives is attributed to the introduction of excessive nitro groups into energetic plasticizers. That is, it was found that abundant nitro groups, when introduced into energetic plasticizers, are advantageous in terms of energy density, but cause the plasticizer to increase in viscosity and polarity, and that such high polarity induces the dissolution of the granular explosive, causing the granular explosive to be morphologically altered.

In addition, intensive and thorough research by the present inventors resulted in the finding that 3,3-dinitroazetidine (DNAZ) itself has a symmetrical structure with synthetic convenience and structural brevity and that the structural regularity makes DNAZ an energetic material that has too high a melting point to use as a plasticizer.

It is therefore an object of the present invention to provide N-substituted 3,3-dinitroazetidine, represented by the following Chemical Formula I, as a high-performance, energetic plasticizer.

It is another object of the present invention to provide a method for preparing the N-substituted 3,3-dinitroazetidine.

It is a further object of the present invention to provide a plasticizer comprising the N-substituted 3,3-dinitroazetidine.

In accordance with an aspect thereof, the present invention provides an N-substituted 3,3-dinitroazetidine represented by the following Chemical Formula I:

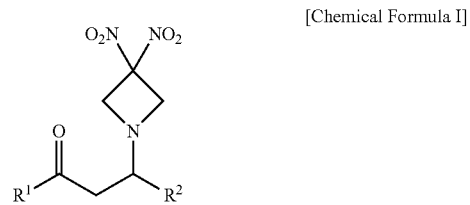

[Chemical Formula I]

wherein $R^1$ and $R^2$ are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom, wherein the substituent of the substituted radicals is selected from the group consisting of alkyl, cycloalkyl, aryl, heteroaryl, alkoxy, thioalkyl, amino, nitro, hydroxy, a halogen atom, and a combination thereof.

In accordance with another aspect thereof, the present invention provides a method for preparing a compound represented by the following Chemical Formula I, comprising: dissolving dinitroazetidine (DNAZ) and/or at least one DNAZ acid salt selected from the group consisting of dinitroazetidine hydrochloride (DNAZ.HCl), dinitroazetidine sulfate (DNAZ.H2SO4), and dinitroazetidine nitrate (DNAZ.HNO3), represented by the following Chemical Formula II, in an organic solvent, and reacting the solution with an α,β-unsaturated carbonyl compound represented by the following Chemical Formula III in the presence of a base:

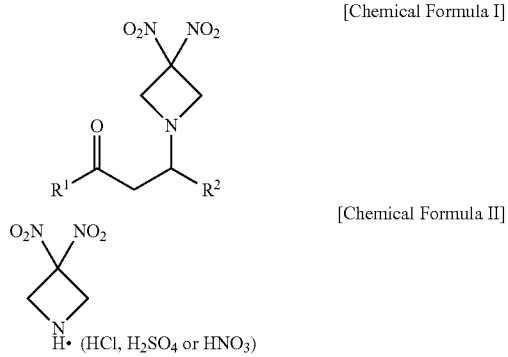

[Chemical Formula I]

[Chemical Formula II]

[Chemical Formula III]

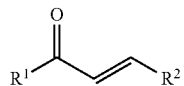

wherein R¹ and R² are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom, wherein the substituent of the substituted radicals is selected from the group consisting of alkyl, cycloalkyl, aryl, heteroaryl, alkoxy, thioalkyl, amino, nitro, hydroxy, a halogen atom, and a combination thereof.

In accordance with a further aspect thereof, the present invention provides a plasticizer comprising the N-substituted 3,3-dinitroazetidine represented by Chemical Formula I.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
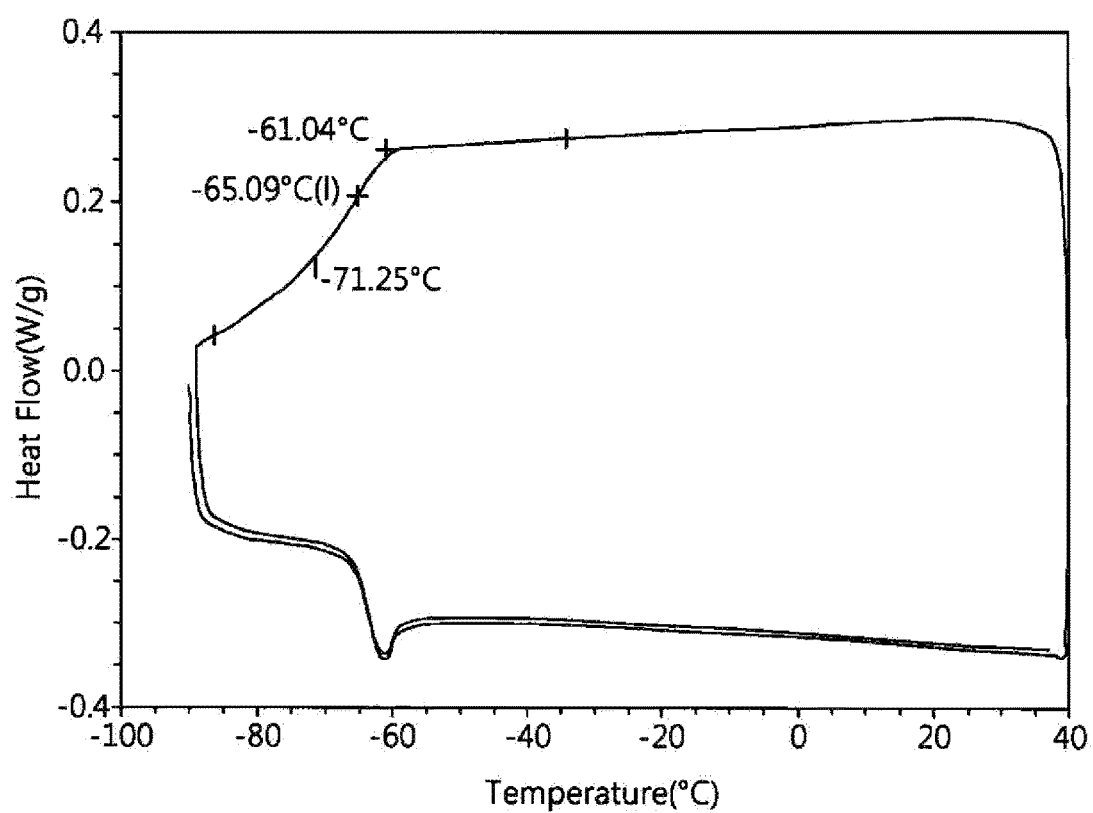
FIG. 1 is a thermal profile of 6-(3,3-dinitroazetidin-1-yl)-2-methylundecan-4one (Example 5), as measured by differential scanning calorimetry (DSC)

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

An aspect of the present invention addresses an N-substituted 3,3-dinitroazetidine represented by the following Chemical Formula I:

[Chemical Formula I]

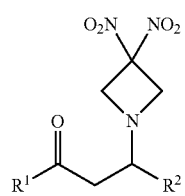

wherein R¹ and R² are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom wherein the substituent of the substituted radicals is selected from the group consisting of alkyl, cycloalkyl, aryl, heteroaryl, alkoxy, thioalkyl, amino, nitro, hydroxy, a halogen atom, and a combination thereof. Preferably, the alkyl radical is a C1-C10 alkyl.

Also, contemplated in accordance with another aspect of the present invention is a method for preparing a compound represented by the following Chemical Formula I, comprising: dissolving dinitroazetidine (DNAZ) and/or at least one DNAZ acid salt selected from the group consisting of dinitroazetidine hydrochloride (DNAZ.HCl), dinitroazetidine sulfate (DNAZ.H2SO4), and dinitroazetidine nitrate (DNAZ.HNO3), represented by the following Chemical Formula II, in an organic solvent, and reacting the solution with an α,β-unsaturated carbonyl compound, represented by the following Chemical Formula III, in the presence of a base:

[Chemical Formula I]

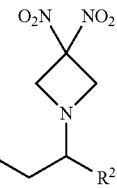

[Chemical Formula II]

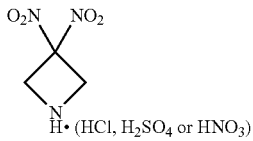

[Chemical Formula III]

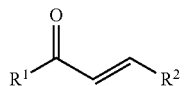

wherein R¹ and R² are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom, wherein the substituent of the substituted radicals is selected from the group consisting of alkyl, cycloalkyl, aryl, heteroaryl, alkoxy, thioalkyl, amino, nitro, hydroxy, a halogen atom, and a combination thereof.

Dinitroazetidine (DNAZ) is structurally symmetric with structural brevity, and thus shows structural regularity. For this reason, DNAZ is an energetic material that has too high a melting point to be used as a plasticizer. In contrast, the N-substituted 3,3-dinitroazetidine according to the present invention can be used as a plasticizer having a high energy density due to the structural stress of the dinitroazetidine moiety. The N-substituted 3,3-dinitroazetidine can be synthesized through a coupling reaction in which 3,3-dinitroazetidine or an acid salt thereof serves as a nucleophile for the α,β-unsaturated carbonyl compound as a substrate. In addition, the α,β-unsaturated carbonyl compound represented by Chemical Formula III is versatile, so that the N-substituent can be controlled to give chemical structures that decrease the melting points of the resulting compounds, thereby minimizing the side effect of dissolving granular explosives.

In the α,β-unsaturated carbonyl compound used in the preparation method, $R^1$ and $R^2$ are each independently alkyl, substituted alkyl, aryl, substituted aryl, arylalkyl, substituted arylalkyl, heteroaryl, substituted heteroaryl, heteroarylalkyl, substituted heteroarylalkyl, hydroxy, nitro, or a halogen atom, wherein the substituent of the substituted radicals is selected from the group consisting of alkyl, cycloalkyl, aryl, heteroaryl, alkoxy, thioalkyl, amino, nitro, hydroxy, a halogen atom, and a combination thereof.

In the preparation method, the organic solvent may be at least one selected from the group consisting of toluene, dichloromethane, chloroform, tetrahydrofuran, diethylether, methanol, ethanol, and propanol.

For use in the preparation method, the base may be at least one selected from the group consisting of potassium hydroxide, lithium hydroxide, sodium hydroxide, rubidium hydroxide, and cesium hydroxide.

In the preparation method, when the reaction mixture is stirred, a tetraalkylammonium halide, such as tetrabutylammonium iodide (TBAI), tetrabutylammonium bromide (TBAB), tetrabutylammonium chloride (TBAC), or the like, may be used as a phase-transition catalyst to increase the reaction rate.

After completion of the reaction, purification by column chromatography may afford the N-substituted 3,3-dinitroazetidine.

A better understanding of the present invention may be obtained through the following examples, which are set forth to illustrate, but are not to be construed as limiting the present invention.

All of the materials used in the following Examples, including potassium hydroxide, tetrabutylammonium iodide, tetrabutylammonium bromide, and toluene, were of reagent grades from Sigma-Aldrich. Dinitroazetidine and a hydrochloride thereof were synthesized as disclosed previously (Kown, Y.-H., U.S. Pat. No. 7,829,729 B2). The α,β-unsaturated carbonyl compounds were synthesized using a method known in the art.

EXAMPLE 1

Synthesis of 3-(3,3-Dinitroazetidin-1-yl)-1-phenyloctan-1-one

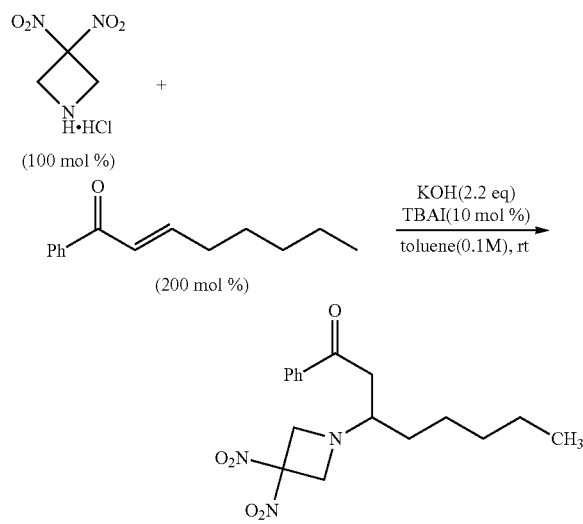

To a solution of the starting material DNAZ.HCl (0.028 g, 0.15 mmol) in toluene (1.5 mL, 0.1 M) were added (E)-1-phenyloct-2-en-1-one (0.06 g, 2 eq), torabutylammonium iodide (0.006 g, 0.1 eq), and potassium hydroxide (0.019 g, 2.2 eq), followed by stirring at room temperature for 24 hrs. After completion of the reaction, column chromatographic purification afforded the title compound as a yellowish oil: yield 74% (0.039 g, 0.11 mmol)

$^1$H NMR (400 MHz, CDCl$_3$) δ 7.96-7.93 (m, 2H), 7.62-7.58 (m, 1H), 7.51-7.47 (m, 2H), 4.15-4.05 (m, 4H), 3.30-3.24 (m, 1H), 3.10-2.95 (m, 2H), 1.51-1.44 (m, 1H), 1.42-1.20 (m, 7H), 0.87 (t, J=6.8 Hz, 3H) HRMS (FAB) calcd for [M+H]$^+$ C$_{17}$H$_{24}$O$_5$N$_3$ 350.1716, found 350.1718.

EXAMPLE 2

Synthesis of 4-(3,3-Dinitroazetidin-1-yl)-6-methylheptan-2-one

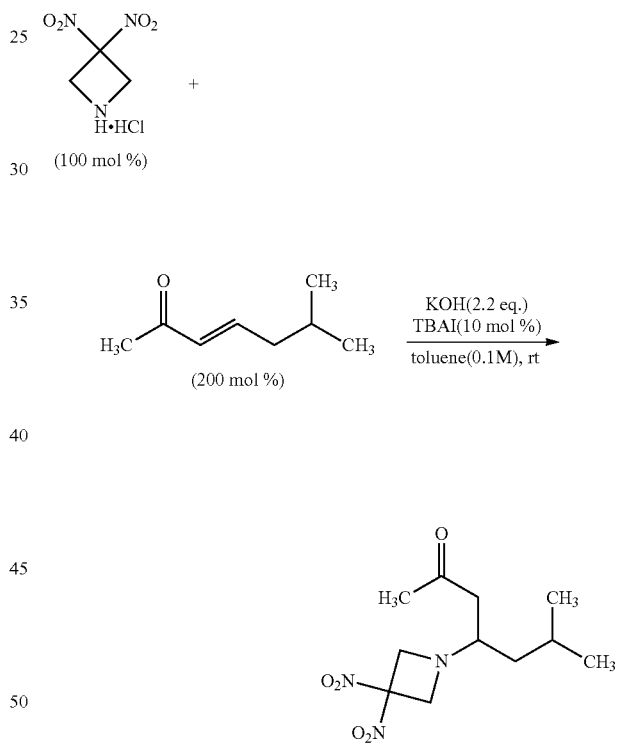

To a solution of the starting material DNAZ.HCl (0.055 g, 0.3 mmol) in toluene (3 mL, 0.1 M) were added (E)-6-methylhept-3-en-2-one (0.075 g, 2 eq), tetrabutylammonium bromide (0.010 g, 0.1 eq), and potassium hydroxide (0.037 g, 2.2 eq), followed by stirring at room temperature for 24 hrs. After completion of the reaction, column chromatographic purification afforded the title compound as a yellowish oil: yield 32% (0.026 g, 0.1 mmol).

$^1$H NMR (400 MHz, CDCl$_3$) δ 4.11-4.02 (m, 4H), 3.12-3.06 (m, 1H), 2.57-2.43 (m, 2H), 2.19 (s, 3H), 1.60-1.50 (m, 1H), 1.19-1.15 (m, 2H), 0.93 (d, J=6.4 Hz, 3H), 0.89 (d, J=6.4 Hz, 3H) HRMS (FAB) calcd for [M+]$^+$ C$_{11}$H$_{20}$O$_5$N$_3$ 274.1403, found 274.1406.

EXAMPLE 3

Synthesis of 2-(3,3-Dinitroazetidin-1-yl)-6-methylheptan-4-one

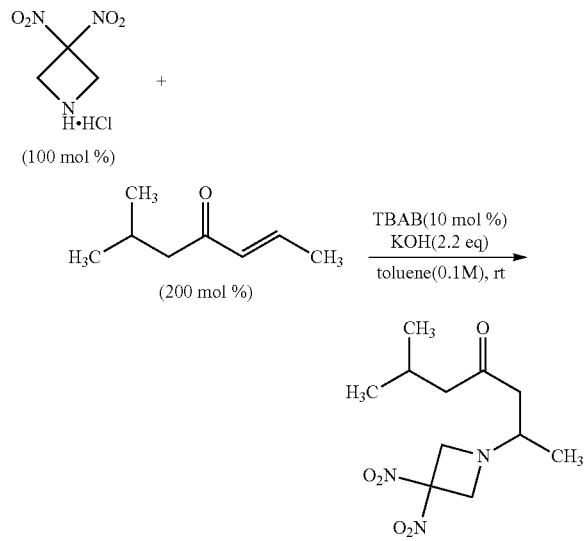

To a solution of the starting material DNAZ.HCl (0.018 g, 0.1 mmol) in toluene (1 mL, 0.1 M) were added [(E)-6-methylhept-2-en-4-one (0.025 g, 2 eq), tetrabutylammonium bromide (0.003 g, 0.1 eq), and potassium hydroxide (0.012 g, 2.2 eq), followed by stirring at room temperature for 24 hrs. After completion of the reaction, column chromatographic purification afforded the title compound as a yellowish oil: yield 84% (0.023 g, 0.08 mmol).

$^1$H NMR (400 MHz, CDCl$_3$) δ 4.11-4.04 (m, 4H), 3.09-3.01 (m, 1H), 2.48-2.33 (m, 2H), 2.28 (d, J=6.8 Hz, 2H), 2.19-2.04 (m, 1H), 1.00 (d, J=6.0 Hz, 3H), 0.91 (d, J=6.4 Hz, 3H), 0.91 (d, J=6.4 Hz, 3H) HRMS (FAB) calcd for [M+H]$^+$ C$_{11}$H$_{20}$O$_5$N$_3$ 274.1403, found 274.1405.

EXAMPLE 4

Synthesis of 6-(3,3-dinitroazetidin-1-yl)-2,8-dimethylnonan-4-one

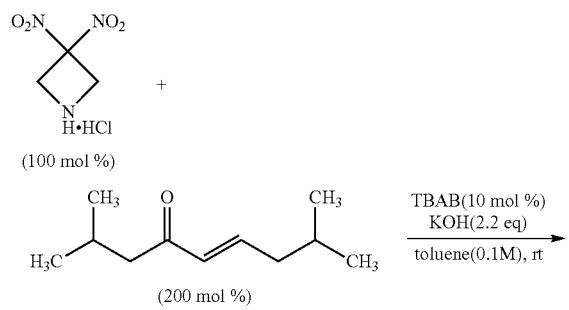

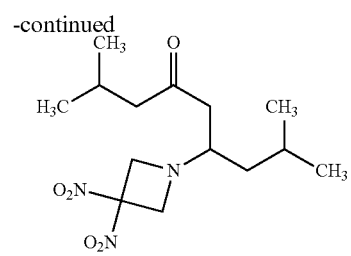

To a solution of the starting material DNAZ.HCl (0.055 g, 0.3 mmol) in toluene (3 mL, 0.1 M) were added (E)-2,8-dimethylnon-5-en-4-one (0.1 g, 2 eq), tetrabutylammonium bromide (0.010 g, 0.1 eq), and potassium hydroxide (0.037 g, 2.2 eq), followed by stirring at room temperature for 24 hrs. After completion of the reaction, column chromatographic purification afforded the title compound as a yellowish oil: yield 80% (0.028 g, 0.12 mmol).

$^1$H NMR (400 MHz, CDCl$_3$) δ 4.11-4.01 (m, 4H), 3.14-3.08 (m, 1H), 2.52-2.38 (m, 2H), 2.30 (d, J=6.8 Hz, 2H), 2.18-2.08 (m, 1H), 1.59-1.49 (m, 1H), 1.18-1.14 (m, 2H), 0.92 (d, J=6.8 Hz, 3H), 0.92 (d, J=6.4 Hz, 3H), 0.91 (d, J=6.4 Hz, 3H), 0.88 (d, J=6.8 Hz, 3H) HRMS (FAB) calcd for [M+H]$^+$ C$_{14}$H$_{26}$O$_5$N$_3$ 316.1872, found 316.1870.

EXAMPLE 5

Synthesis of 6-(3,3-Dinitroazetidin-1-yl)-2-methylundecan-4-one

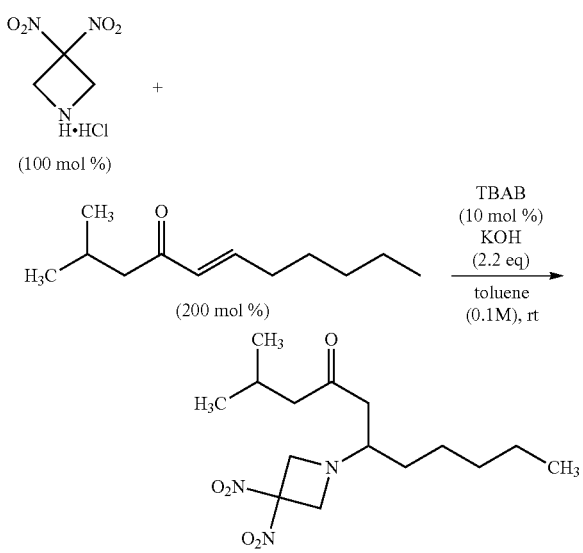

To a solution of the starting material DNAZ.HCl (0.037 g, 0.2 mmol) in toluene (2 mL, 0.1 M) were added (E)-2-methylundec-5-en-4-one (0.073 g, 2 eq), tetrabutylammonium bromide (0.006 g, 0.1 eq), and potassium hydroxide (0.025 g, 2.2 eq), followed by stirring at room temperature for 36 hrs. After completion of the reaction, column chromatographic purification afforded the title compound as a yellowish oil: yield 53% (0.035 g, 0.11 mmol).

$^1$H NMR (400 MHz, CDCl$_3$) δ 4.11-4.02 (m, 4H), 3.06-3.01 (m, 1H), 2.53-2.35 (m, 2H), 2.30 (d, J=6.8 Hz, 2H), 2.17-2.07 (m, 1H), 1.41-1.35 (m, 1H), 1.31-1.19 (m, 7H), 0.91 (d, J=6.8 Hz, 6H), 0.88 (t, J=6.4 Hz, 3H) HRMS (FAB) calcd for [M+H]+ $C_{15}H_{28}O_5N_3$ 330.2029, found 330.2030.

EXAMPLE 6

Synthesis of 6-Cyclohexyl-4-(3,3-dinitroazetidin-1-yl)hexan-2-one

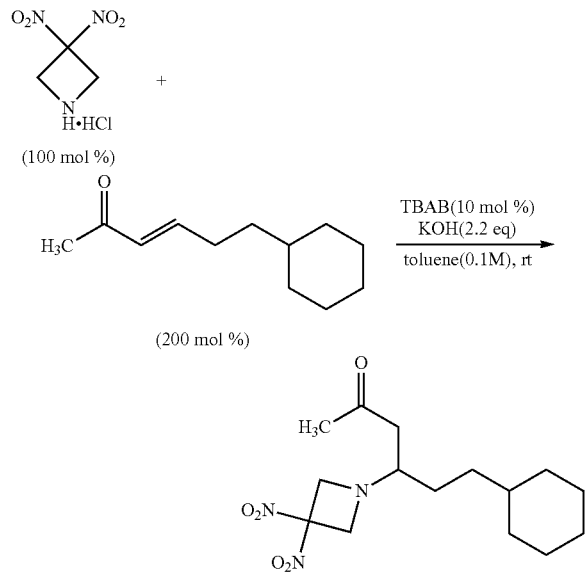

To a solution of the starting material DNAZ.HCl (0.037 g, 0.2 mmol) in toluene (2 mL, 0.1 M) were added (E)-6-cyclohexylhex-3-en-2-one (0.072 g, 2 eq), tetrabutylammonium bromide (0.006 g, 0.1 eq), and potassium hydroxide (0.025 g, 2.2 eq), followed by stirring at room temperature for 24 hrs. After completion of the reaction, column chromatographic purification afforded the title compound as a yellowish oil: yield 65% (0.043 g, 0.13 mmol).

$^1$H NMR (400 MHz, CDCl$_3$) δ 4.10-4.03 (m, 4H), 3.03-2.97 (m, 1H), 2.57-2.40 (m, 2H), 2.18 (s, 3H), 1.68-1.64 (m, 5H), 1.45-1.36 (m, 1H), 1.34-1.06 (m, 7H), 0.89-0.79 (m, 2H) HRMS (FAB) calcd for [M+H]+ $C_{15}H_{26}O_5N_3$ 328.1872, found 328.1869.

EXAMPLE 7

Synthesis of 8-Cyclohexyl-6-(3,3-dinitroazetidin-1-yl)-2-methyloctan-4-one

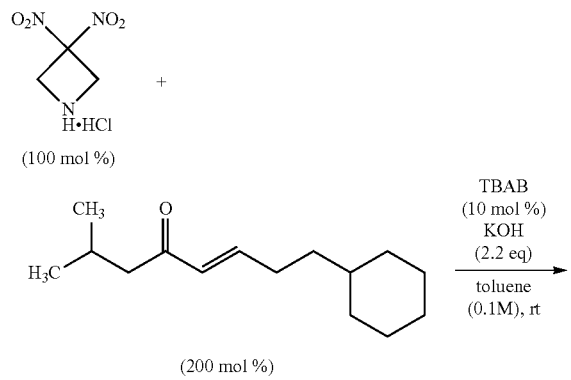

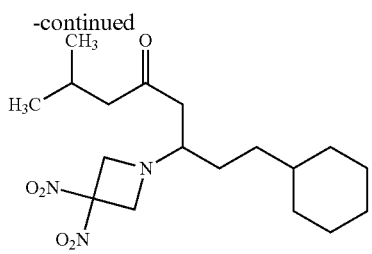

To a solution of the starting material DNAZ.HCl (0.057 g, 0.31 mmol) in toluene (3.1 mL, 0.1 M) were added (E)-8-cyclohexyl-2-methyloct-5-en-4-one (0.161 g, 2 eq), tetrabutylammonium bromide (0.01 g, 0.1 eq), and potassium hydroxide (0.038 g, 2.2 eq), followed by stirring at room temperature for 48 hrs. After completion of the reaction, column chromatographic purification afforded the title compound as a yellowish oil: yield 74% (0.086 g, 0.23 mmol).

$^1$H NMR (400 MHz, CDCl$_3$) δ 4.10-4.02 (m, 4H), 3.05-2.99 (m, 1H), 2.52-2.34 (m, 2H), 2.29 (d, J=7.2 Hz, 2H), 2.17-2.07 (m, 1H), 1.72-1.61 (m, 5H), 1.44-1.36 (m, 1H), 1.33-1.05 (m, 7H), 0.91 (d, J=6.8 Hz, 6H), 0.89-0.80 (m, 2H) HRMS (FAB) calcd for [M+H]+ $C_{18}H_{32}O_5N_3$ 370.2342, found 370.2339.

EXAMPLE 8

Glass Transition Temperature and Thermal Decomposition for Energetic Plasticizer Of the N-substituted 3,3-dinitroazetidines synthesized above, 6-(3,3-dinitroazetidin-1-yl)-2-methylundecan-4-one (Example 5) and 8-cyclohexyl-6-(3,3-dinitroazetidin-1-yl)-2-methyloctan-4-one (Example 7) were measured for glass transition temperature (Tg) and thermal decomposition temperature in order to examine whether the compounds have physical properties suitable for use as energetic plasticizers.

Glass transition temperatures were measured by differential scanning calorimetry (DSC, Differential Scanning Calorimeter, DSC821$^e$ Mettler Toledo or Q2000, TA Instruments) while thermal decomposition temperatures were determined by thermogravimetric analysis (TGA, SDTA851$^e$, Mettler Toledo, or Q600, TA Instruments). For these analyses, the samples were heated with a temperature increase of 10° C./min under a nitrogen atmosphere.

Figure 2:
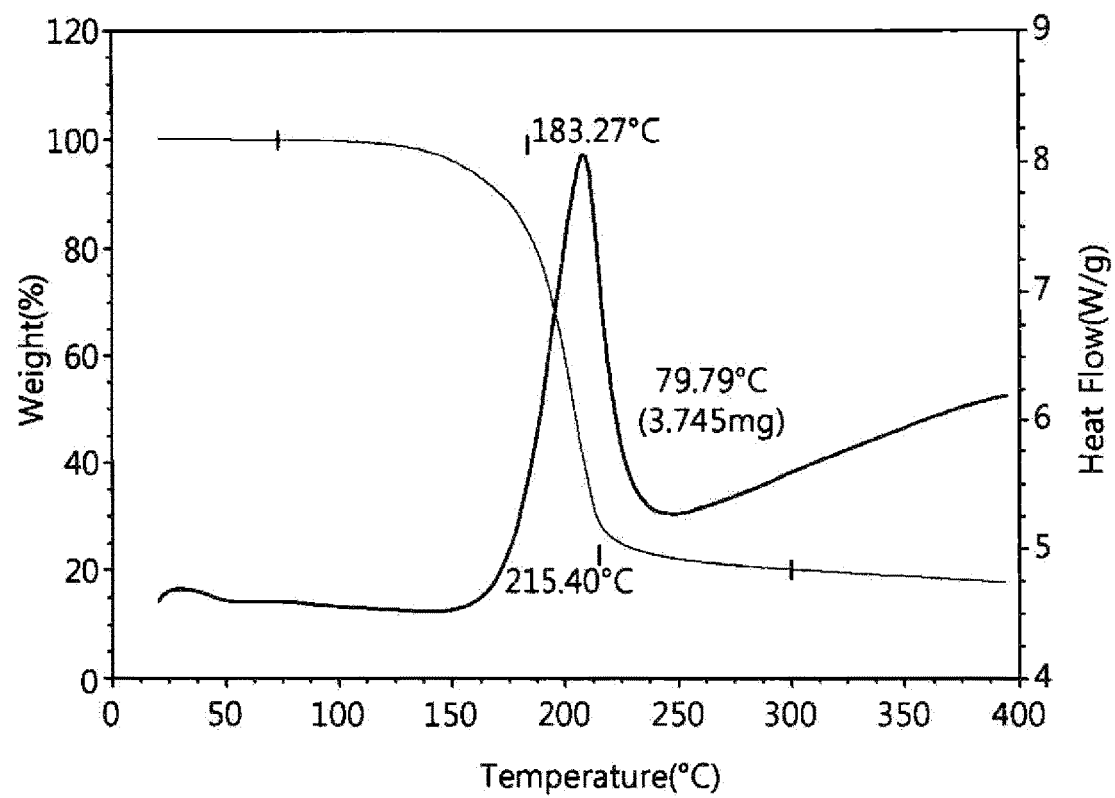
FIG. 2 is a thermal profile of 6-(3,3-dinitroazetidin-1-yl)-2-methylundecan-4-one (Example 5), as measured by thermogravimetric analysis (TGA)
Figure 3:
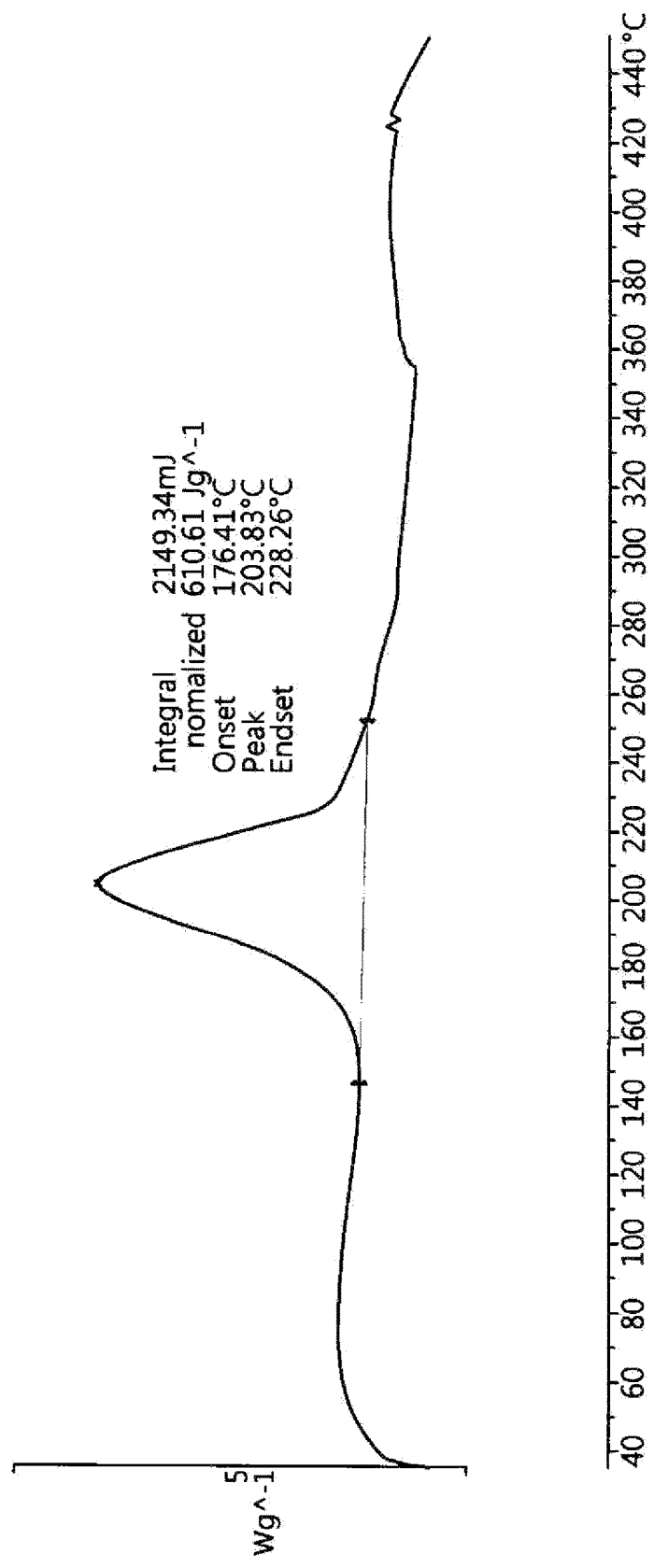
FIG. 3 is a thermal profile of 8-cyclohexyl-6-(3,3-dinitroazetidin-1-yl)-2-methyloctan-4-one (Example 7), as measured by differential scanning calorimetry (DSC)
Figure 4:
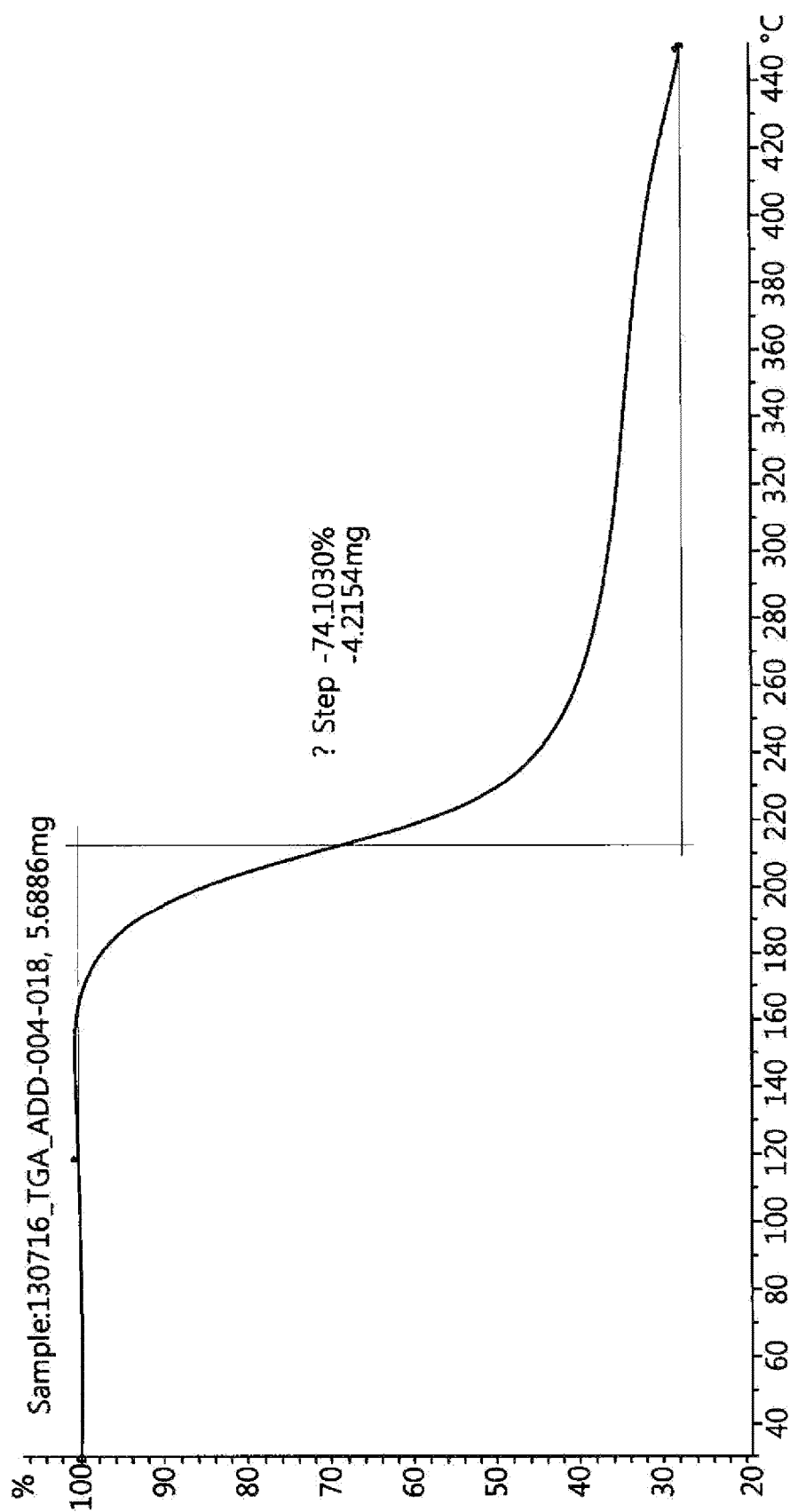
FIG. 4 is a thermal profile of 8-cyclohexyl-6-(3,3-dinitroazetidin-1-yl)-2-methyloctan-4-one (Example 7), as measured by thermogravimetric analysis (TGA)
Figure 5:
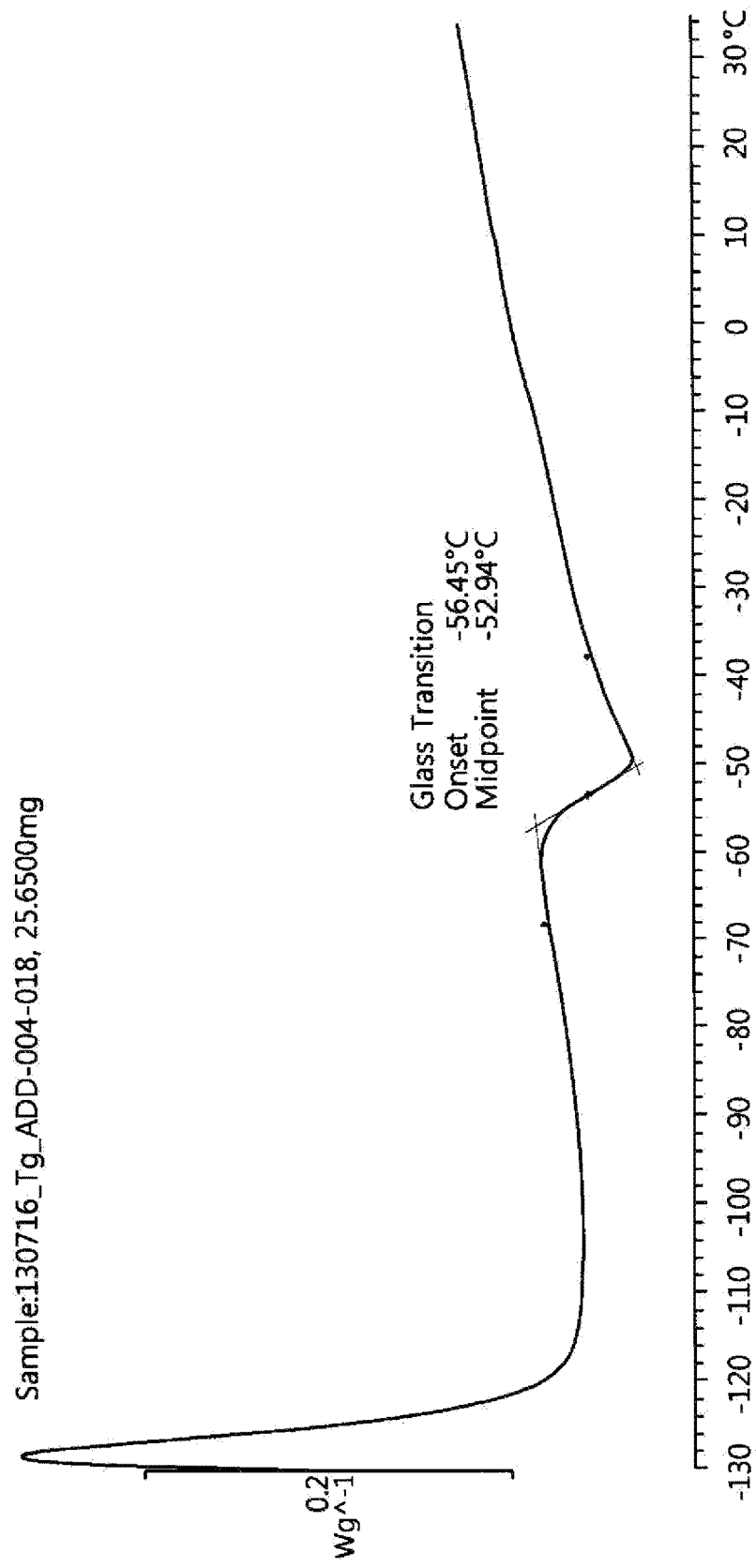
FIG. 5 is a thermal profile showing the glass transition temperature (Tg) of 8-cyclohexyl-6-(3,3-dinitroazetidin-1-yl)-2-methyloctan-4-one (Example 7).

The results are depicted in FIGS. 1 to 5. As can be seen from the data on the glass transition temperature and thermal decomposition, the N-substituted 3,3-dinitroazetidine of the present invention is identified as being suitable for use as an energetic plasticizer.

As described above, the N-substituted 3,3-dinitroazetidine according to the present invention can be used as an energetic plasticizer that takes advantage of the structural stress of the energetic material dinitroazetidine in increasing the energy density thereof, and which can be modified with the N-substituent to reduce the melting point thereof and to minimize the side effect of dissolving granular explosives. Hence, the N-substituted 3,3-dinitroazetidine of the present invention has physical properties suitable for use as an energetic plasticizer and can increase the energy density of plastic-bonded explosives and reduce the side effect of dissolving granular explosives as much as possible.

Therefore, the N-substituted 3,3-dinitroazetidine of the present invention can be used as a high-performance, energetic plasticizer in which abundant nitro groups of conventional energetic plasticizers are converted into a ring energy.

As described hitherto, the N-substituted 3,3-dinitroazetidine, represented by Chemical Formula I, according to the present invention can be used as a plasticizer.

Also, the novel preparation method of N-substituted 3,3-dinitroazetidine according to the present invention is characterized by a coupling reaction.

Further, the plasticizer comprising the N-substituted 3,3-dinitroazetidine of Chemical Formula I in accordance with the present invention can increase the energy density of plastic-bonded explosives, and nitro groups comprised in conventional energetic plasticizer of Chemical Formula 1, 2 and 3 are converted into a ring energy, thus minimizing the side effect of solubilizing granular explosives.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

As described above, optimal embodiments of the present invention have been disclosed in the drawings and the specification. Although specific terms have been used in the present specification, these are merely intended to describe the present invention, and are not intended to limit the meanings thereof or the scope of the present invention described in the accompanying claims. Therefore, those skilled in the art will appreciate that various modifications and other equivalent embodiments are possible from the embodiments. Therefore, the technical scope of the present invention should be defined by the technical spirit of the claims.

What is claimed is:

1. N-substituted 3,3-dinitroazetidine, represented by the following Chemical Formula I:

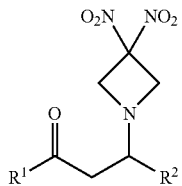

[Chemical Formula I]

wherein $R^1$ and $R^2$ are each independently an alkyl of C1~C10, a substituted alkyl of C1~C10, an aryl of C6~C12, or a substituted aryl of C6~C12 wherein the substituent of the substituted radicals is selected from the group consisting of an alkyl of C1~C4, a cycloalkyl of C4~C12, an aryl of C6~C12, and a combination thereof.

2. A method for preparing a compound represented by the following Chemical Formula I, comprising:

dissolving dinitroazetidine (DNAZ) and/or at least one DNAZ acid salt selected from the group consisting of dinitroazetidine hydrochloride (DNAZ.HCl), dinitroazetidine sulfate (DNAZ.H$_2$SO$_4$), and dinitroazetidine nitrate (DNAZ.HNO$_3$), represented by the following Chemical Formula II, in an organic solvent; and reacting the solution with an α,β-unsaturated carbonyl compound represented by the following Chemical Formula III in the presence of a base:

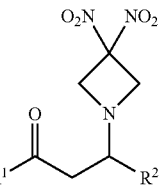

[Chemical Formula I]

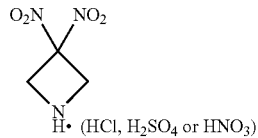

[Chemical Formula II]

[Chemical Formula III]

wherein $R^1$ and $R^2$ are each independently an alkyl of C1~C10, a substituted alkyl of C1~C10, an aryl of C6~C12, or a substituted aryl of C6~C12, wherein the substituent of the substituted radicals is selected from the group consisting of an alkyl of C1~C4, a cycloalkyl of C4~C12, an aryl of C6~C12, and a combination thereof.

3. A plasticizer, comprising the N-substituted 3,3-dinitroazetidine, represented by Chemical Formula I, of claim 1.

* * * * *